United States Patent [19]

Hodgson

[11] Patent Number: 4,619,266

[45] Date of Patent: Oct. 28, 1986

[54] ELECTRODE ARRAY FOR MUSCLE STIMULATION AND RECORDING

[76] Inventor: John A. Hodgson, 42 Shirley Avenue, Shirley, Southampton, England

[21] Appl. No.: 608,446

[22] Filed: May 9, 1984

[30] Foreign Application Priority Data

May 11, 1983 [GB] United Kingdom ................. 8313005
Nov. 22, 1983 [GB] United Kingdom ................. 8331149

[51] Int. Cl.<sup>4</sup> ......................... A61B 5/04; A61N 1/04
[52] U.S. Cl. .................................... 128/639; 128/733; 128/798
[58] Field of Search ............................. 128/639–641, 128/643, 644, 693, 733, 734, 783, 798, 799, 802, 421–423 R

[56] References Cited

U.S. PATENT DOCUMENTS

| | | | |
|---|---|---|---|
| 3,386,445 | 6/1968 | McDonald | 128/798 |
| 3,720,209 | 3/1973 | Bolduc | 128/639 |
| 3,750,649 | 8/1973 | Severinghaus | 128/734 |
| 3,888,240 | 6/1975 | Reinhold, Jr. et al. | 128/644 |
| 3,998,213 | 12/1976 | Price | 128/644 |
| 4,375,219 | 3/1983 | Schmid | 128/639 |

FOREIGN PATENT DOCUMENTS

| | | | |
|---|---|---|---|
| 2735050 | 2/1979 | Fed. Rep. of Germany | 128/640 |
| 1498893 | 1/1975 | United Kingdom . | |
| 1566211 | 11/1977 | United Kingdom . | |

OTHER PUBLICATIONS

Romanchishen, "Electrode System ... Gland", Biomed Eng., vol. 12, No. 2., Mar.–Apr. 1978, pp. 95–95.

Primary Examiner—Lee S. Cohen
Attorney, Agent, or Firm—Larson and Taylor

[57] ABSTRACT

A flexible backing pad bears a spaced pair of recording electrodes at right angles to a spaced pair of stimulating electrodes. The recording electrodes may have associated signal ground electrodes. The array is attachable to mammalian skin over a muscle so that the recording electrodes pick up electrical muscle activity. A resulting signal is fed to processing apparatus which generates a stimulating signal and feeds it to the stimulating electrodes. The electrode array is arranged to minimize direct influence of the stimulating signal on the recording electrodes.

10 Claims, 3 Drawing Figures

ELECTRODE ARRAY FOR MUSCLE STIMULATION AND RECORDING

BACKGROUND OF THE INVENTION

This invention relates to an electrode array, and more particularly to one which may be applied to a mammalian body and used for muscle stimulation and for recording electrical activity.

A previous U.K. patent application (GB No. 2 098 489 A—Signal Processing Apparatus) described a device which may be used to record electrical activity (electromyograms) from a muscle in a mammalian body and to apply an electrical stimulus to activate that same muscle at a frequency proportional to the average amplitude of the electromyogram. A problem with such apparatus, however, is that the natures of the two signals are such that they can interact and create an undesirable artifact on the recorded signal. The present invention seeks to provide an electrode array intended to reduce such interaction.

SUMMARY OF THE INVENTION

According to the present invention, an electrode array comprises two pairs of electrodes, adapted for placement on the skin of a mammal overlying a muscle, in electrical contact therewith, the two electrodes of each pair being spaced from each other along respective axes of the array, the axis of one electrode pair being generally at right angles to that of the other pair.

Preferably, the electrodes of one pair (intended for recording electrical activity in the muscle) are spaced equidistantly from the other two electrodes (intended for providing a stimulating current to the muscle). In a preferred embodiment, an additional electrode or electrodes is provided, arranged to provide a signal ground for the recording electrodes.

DESCRIPTION OF THE PREFERRED EMBODIMENT

Figure 1:
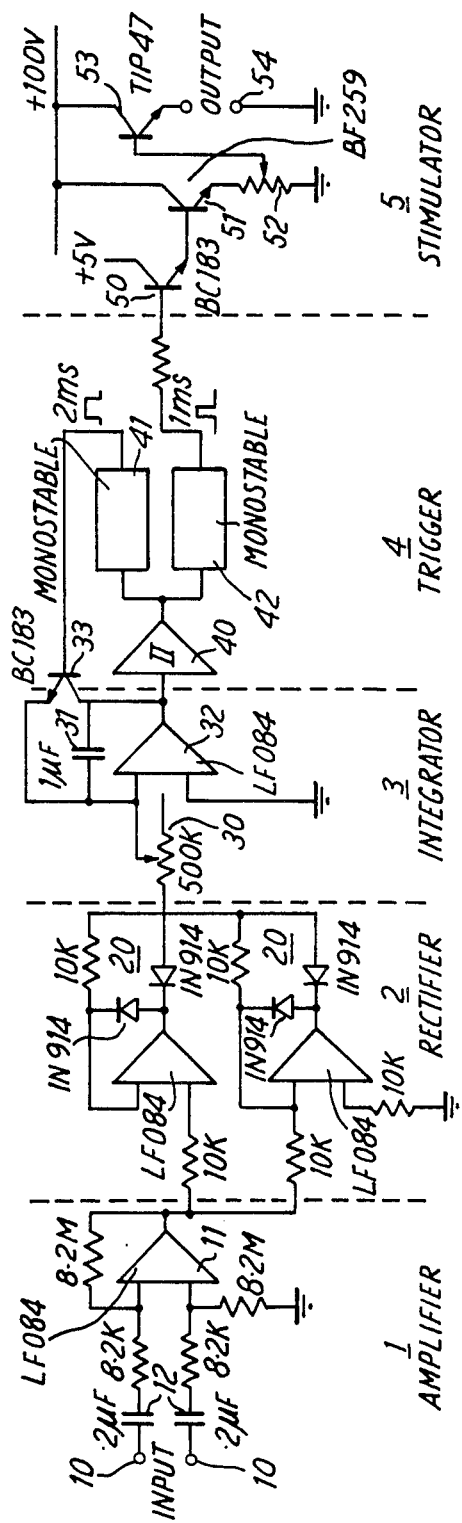
FIG. 1 is a circuit diagram of signal processing apparatus.

The electrode pad may be used with the apparatus described in patent application GB No. 2 098 489 A, which is incorporated herein by reference, and FIG. 1 of which is reproduced as FIG. 1 of this specification. That apparatus is adapted for use in receiving a first signal from a human body (for example), and processing that signal to produce a control signal which can be used to control a bodily response. One example of where the apparatus may be used is with a stroke patient suffering from flaccid paralysis. Some slight activity is detected in an affected muscle as an electrical signal, which signal serves as the first signal which is input to the apparatus. The signal is then processed in the apparatus, to provide a control signal which is fed directly back to the same muscle to produce a significant force.

Referring to FIG. 1, the apparatus shown therein comprises five stages arranged in series—namely an amplifier stage 1, a rectifier stage 2, an integrator stage 3, a trigger stage 4, and a stimulator stage 5, which latter stage is the output stage of the device.

The amplifier stage is arranged to receive a first input signal on terminals 10, which input signal is fed to a differential amplifier 11. The amplifier 11 is arranged to afford a high input impedance, and in the illustrated example, it has a gain of approximately 1,000. Capacitors 12 serve to A.C. couple the input terminals 10 to the amplifier 11.

The output of the amplifier 11 is fed to two parallel half-stages 20 of the rectifier stage 2. The circuit configurations of the two half-stages 20 are almost identical, and each half-stage is arranged to provide substantially unity gain. However, one of the half-stages 20 is arranged to pass only positive signal portions, whilst the other half-stage is arranged to pass only negative signal portions. Also, one of the half-stages is arranged to provide inversion of the input signal, while the other half-stage is arranged in a non-inverting manner.

The rectified signal appearing at the output of the rectifier stage 2 is fed to a variable resistance 30 at the input of the integrator stage 3. The variable resistance 30, together with a capacitance 31, define an R.C. time constant of an operational amplifier 32, which is arranged as an integrator. A transistor 33, arranged as a switch, is provided to discharge the capacitance 31, and thereby reset the integrator stage 3.

The output of the integrating amplifier 32 is fed as an input to a trigger 40 of the trigger stage 4. The trigger 40 has offset switching thresholds, such that it changes state when the output of the integrating amplifier 32 reaches a first predetermined limit value, and changes state again when the output of the integrating amplifier 32 falls below a second predetermined limit value, which is greater in magnitude than the first limit value.

The output of the trigger 40 is connected to inputs of respective monostable devices 41 and 42.

The first monostable device 41 is arranged to respond to a change of state of the trigger 40 corresponding to the output of the integrating amplifier 32 reaching said first limit value, whereupon the monostable device 41 emits a 2 mS (for example) pulse, which is operative to switch on the switching transistor 33, and thereby reset the integrator stage 3.

The second monostable device 42 responds in a similar manner to the monostable device 41, but emits a shorter pulse of 1 mS duration, which pulse is fed to an input transistor 50 of the stimulator stage 5. All the circuitry up to and including the input transistor 50 is powered from low voltage—in this example, +5 volts.

The input transistor 50 in turn drives a further transistor 51, which is powered by a relatively high potential source—in this example, +100 volts. A variable resistance 52 is connected in the emitter path of the transistor 51, and an input to an output transistor 53 is tapped from the variable resistance 52 such that, upon a 1 mS pulse appearing at the base of the input transistor 50, the transistors 51 and 53 are switched on accordingly, such that a corresponding 1 mS pulse appears at output terminals 54 in the collector path of the output transistor 53. The value of the output pulse on the terminals 54 depends upon the selective setting of the variable resistance 52, and may be in the range substantially 0–100 volts.

Figure 2:
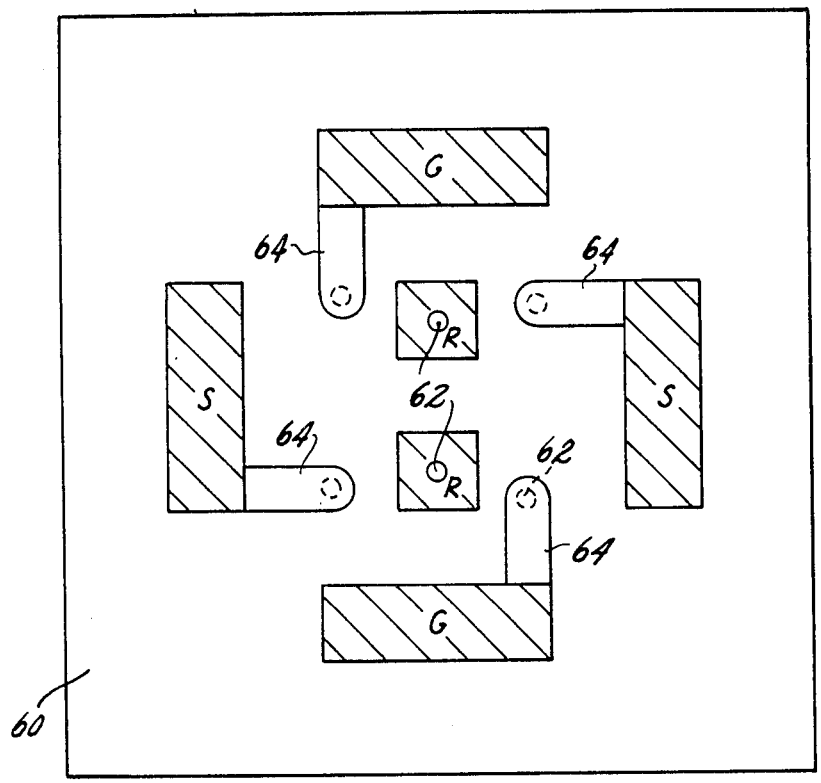
FIG. 2 is a plan view of the front side of the pad.
Figure 3:
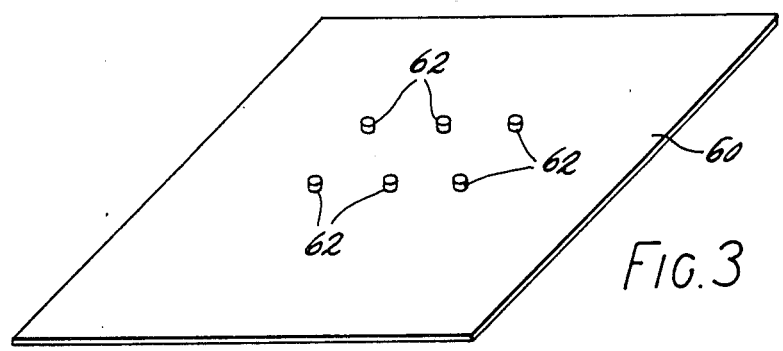
FIG. 3 is an isometric view of the rear side of the pad.

Referring to FIGS. 2 and 3, the electrode pad comprises a flexible non-conductive backing sheet 60, e.g. of a foam plastics material. In use, the sheet 60 may be held in place on the skin of a mammal, overlying a muscle, by a non-conductive adhesive such as those used on adhesive dressings. Alternatively the pad may be held in place with straps.

Electrodes R, G and S are mounted on the front surface of the sheet 60. They are preferably manufactured from a flexible material (e.g. conductive silicon rubber). The spaced pair of electrodes R are intended for recording muscle activity, and in practice would be connected to the differential inputs 10 of the circuitry described in patent application GB No. 2 098 489 A. It will be appreciated that other circuitry could be used instead. The pair of electrodes S are intended for muscle stimulation and are somewhat larger. They are spaced apart one on each side of the electrode pair R, on an axis at right angles thereto, and equidistant therefrom. In practice, they would be connected across the output terminals 54 shown in GB No. 2 098 489 A. The two electrodes G are intended to provide signal ground points for the circuitry connected to the recording electrodes R. They are on the same axis as the electrodes R, though spaced similarly to the electrodes S. Alternativey, the electrodes G could be arranged so that each surrounded its respective electrode R, or there could be a single electrode G surrounding both electrodes R. This has the advantage of assisting equal current distribution to each electrode R. However, the electrodes G are optional, since where differential recording is used, one of the stimulating electrodes S may provide a signal ground for the recording electronics.

With the arrangement of the electrodes R and S just described, current flow from one stimulating electrode S to the other induces approximately equal potential or current changes in each of the recording electrodes R. This arrangement therefore minimises the artifacts on the recorded signal caused by interaction between the electrodes R and S.

Electrical connections may be made to the electrodes R, S and G by means of conductive pegs 62 passing through holes in the backing sheet 60 and in the respective electrodes. The pegs may be electrically connected to the electrodes, or moulded as integral parts of the material of the electrodes. The pegs 62 attached to the electrodes R pass through the main parts of the electrodes. However, the pegs 62 connected to the electrodes S and G are attached to connecting tabs 64 of the respective electrodes, which are covered with an insulating material so as not to make contact with the skin. This provides a neat cluster of pegs 62 in the central region of the pad, to which a suitable multi-way connector can be connected. Alternatively, provision may be made on the electrodes or on the backing to hold electronic circuitry in close proximity to and directly connected to the electrodes.

Electrical contact with the skin may be improved by the application of a conductive substance to the electrodes. This substance would preferably also act as an adhesive to hold the electrode in position on the skin. An appropriate adhesive would be a hypoallergenic copolymer acrylic.

While the invention has been illustrated above by reference to a preferred embodiment, it will be understood by those skilled in the art that various changes may be made without departing from the spirit and scope of the invention, and it is intended to cover all such changes and modifications by the appended claims.

I claim:

1. Apparatus for stimulating and recording electrical activity in a muscle in a mammalian body, said apparatus comprising an electrode array connected to a signal processing apparatus, said electrode array comprising a pair of recording electrodes and a pair of stimulating electrodes, means for mounting said electrodes in fixed, spaced relationship, both pairs of electrodes being adapted for placement on the skin of a mammal overlying a muscle, in electrical contact therewith, the two electrodes of each pair being spaced from each other along respective axes of the array, and the axis of one electrode pair being generally at right angles to that of the other pair; and the signal processing apparatus comprising means for receiving a signal from the recording electrodes, means for processing the signal to produce a control signal for controlling a bodily response; and means for feeding the control signal to the stimulating electrodes.

2. An electrode array according to claim 1 wherein each electrode of the recording pair is equidistant from the electrodes of the stimulating pair.

3. An electrode array according to claim 1 wherein the electrodes of each pair are symmetrically arranged and the recording electrodes are more closely spaced.

4. An electrode array according to claim 1 wherein at least one additional electrode is provided, said additional electrode being mounted by said mounting means in spaced relationship to said recording electrodes and said stimulating electrodes and being electrically connected to said signal processing means so as to provide a signal ground for the recording electrodes.

5. An electrode array according to claim 4 wherein there are two signal ground electrodes on the same axis as the recording electrodes.

6. An electrode array according to claim 4 wherein there are two signal ground electrodes, each surrounding a respective recording electrode.

7. An electrode array according to claim 1 wherein said mounting means includes a flexible non-conductive backing sheet to which the electrodes are mounted.

8. An electrode array according to claim 7 wherein the backing sheet is provided with means for attaching it to the skin of an animal.

9. An electrode array according to claim 7 including conductive pegs, wherein the backing sheet is apertured and respective pegs pass through respective apertures and are connected to respective electrodes.

10. An electrode array according to claim 1 wherein the electrodes are flexible.

* * * * *